United States Patent [19]

Mifune et al.

[11] Patent Number: 4,634,660

[45] Date of Patent: Jan. 6, 1987

[54] DEVELOPMENT-PROCESSING METHOD FOR SILVER HALIDE PHOTOGRAPHIC LIGHT-SENSITIVE MATERIAL

[75] Inventors: Hiroyuki Mifune; Koki Nakamura; Shoji Ishiguro, all of Kanagawa, Japan

[73] Assignee: Fuji Photo Film Co., Ltd., Kanagawa, Japan

[21] Appl. No.: 732,819

[22] Filed: May 10, 1985

Related U.S. Application Data

[63] Continuation of Ser. No. 542,925, Oct. 18, 1983, abandoned.

[30] Foreign Application Priority Data

Oct. 18, 1982 [JP] Japan ................................ 57-182606

[51] Int. Cl.$^4$ ................................ G03C 5/30
[52] U.S. Cl. ................................ 430/375; 430/376; 430/436; 430/438; 430/439; 430/614; 430/423; 430/445; 430/446; 430/600; 430/603; 430/611
[58] Field of Search ............... 430/445, 446, 600, 603, 430/611, 613, 375, 376, 436, 438, 439, 614, 423

[56] References Cited

U.S. PATENT DOCUMENTS 3,295,976  1/1967  Abbott et al. ........................ 430/379

Primary Examiner—Won H. Louie
Attorney, Agent, or Firm—Sughrue, Mion, Zinn, Macpeak & Seas

[57] ABSTRACT

In the presence of a novel antifoggant represented by the general formula (I), a silver halide photographic material which has at least one light-sensitive silver halide emulsion layer on a support is development-processed. The developing solution is one containing both dihydroxybenzenes and 3-pyrazolidones, a developing solution containing both dihydroxybenzenes and aminophenoles, or a developing solution containing a primary aromatic amine developer to suppress markedly fog generation at much reduced sacrifice of sensitivity:

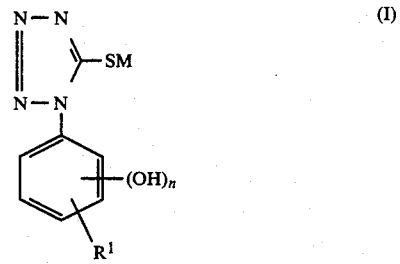

wherein M represents a hydrogen atom, an alkali metal atom, NH$_4$ or a mercapto group-protecting moiety which can be split-off in the presence of an alkali; n represents 1, 2 or 3; R$^1$ represents a hydrogen atom or —COOR$^2$; and R$^2$ represents a hydrogen atom, an alkali metal atom, NH$_4$, or an unsubstituted or substituted alkyl, aryl or aralkyl group.

46 Claims, No Drawings

DEVELOPMENT-PROCESSING METHOD FOR SILVER HALIDE PHOTOGRAPHIC LIGHT-SENSITIVE MATERIAL

This is a continuation of application Ser. No. 06/542,925, filed Oct. 18th, 1983, now abandoned.

FIELD OF THE INVENTION

The present invention relates to a development-processing method for a silver halide photographic light-sensitive material. In greater detail this invention relates to a development-processing method in which fog generation is suppressed.

BACKGROUND OF THE INVENTION

The generation of developmental fog is a phenomenon wherein densities in unexposed areas of a silver halide photographic light-sensitive material (which is abbreviated as "sensitive material" hereinafter) are increased by development-processing. This phenomena is more apt to generate more fog the higher the sensitivity of the sensitive material, the longer the sensitive material is stored, and the higher the temperature and the humidity of an atmosphere in which the sensitive material is stored. However, it is desirable to reduce the generation of developmental fog because it causes deterioration of photographic properties, e.g., lowering of image contrast, etc.

In order to suppress the generation of developmental fog, a means of adding a so-called antifoggant to a sensitive material or a developing solution has been employed, and a great number of compounds are known to function as antifoggants. Among those compounds, 1-phenyl-5-mercaptotetrazole is especially famous as an antifoggant. However, such a compound frequently causes a considerable decrease in sensitivity. Further, 1-phenyl-5-mercaptotetrazole derivatives whose phenyl group is substituted with two carboxyl groups are also known to function as the antifoggant, as described in U.S. Pat. No. 3,266,897. However, as can be seen in the examples of such a patent specification, those derivatives can make only small contribution to the prevention of developmental fog generated in sensitive materials which are stored in an atmosphere of high temperature and high humidity.

Furthermore, U.S. Pat. No. 4,328,302 discloses 1-phenyl-5-mercaptotetrazole derivatives whose phenyl group have certain substituents. However, such an invention relates to an improvement in quality of half tone dots in infectious development and to prevention against generation of fringe and therefore, it differs entirely from the spirit of this invention.

SUMMARY OF THE INVENTION

A primary object of the present invention is to provide a development-processing method which does not have the above-described defects.

Another object of the present invention is to provide a development-processing method which can effectively suppress the generation of developmental fog while diminishing the decrease in sensitivity.

A further object of the present invention is to provide a development-processing method which makes it possible to suppress developmental fog with a reduced decrease in sensitivity even in a sensitive material which has been stored under high temperature and high humidity.

The above-described objects are attained by carrying out the development-processing of a silver halide photographic material, which has at least one light-sensitive silver halide emulsion layer on a support, in the presence of a compound represented by the following general formula (I) using a developing solution containing both dihydroxybenzenes and 3-pyrazolidones, a developing solution containing both dihydroxybenzenes and aminophenols, or a developing solution containing a primary aromatic amine developer:

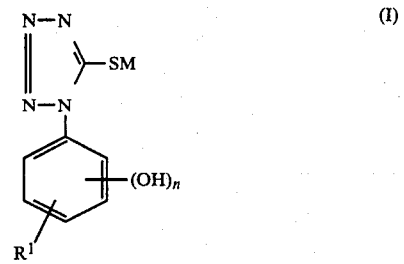

wherein M represents a hydrogen atom, an alkali metal atom, $NH_4$ or a mercapto group-protecting moiety which can be split-off in the presence of an alkali; n represents 1, 2 or 3; $R^1$ represents a hydrogen atom or $-COOR^2$; and $R^2$ represents a hydrogen atom, an alkali metal atom, $NH_4$, or an unsubstituted or substituted alkyl, aryl or aralkyl group.

DETAILED DESCRIPTION OF THE INVENTION

In the foregoing general formula (I), an alkali metal atom represented by M is, e.g., Na, K, etc.; and a mercapto group-protecting moiety represented by M, which can be split-off in the presence of an alkali, includes $-COR^3$, $-COOR^3$, $-CH_2CH_2COOR^3$, $-CH_2CH_2COR^3$, $-CH_2CH_2CONR^3R^4$, $-CH_2CH_2CN$, $-CH_2CH_2SO_2R^3$ and the like. Therein, substituents $R^3$ and $R^4$ each represents a hydrogen atom, or an unsubstituted or substituted alkyl, aryl or aralkyl group, which preferably contains up to 20 carbon atoms in total and has specific examples including methyl group, ethyl group, phenyl group, nitrophenyl group, chlorophenyl group, benzyl group, phenetyl group and so on.

Particularly preferably, M represents a hydrogen atom, an alkali metal atom or $NH_4$.

n represents 1, 2 or 3, preferably 1 or 2.

$R^2$ in $-COOR^2$ represented by the substituent $R^1$ includes a hydrogen atom, an alkali metal atom (e.g., Na, K, etc.), $NH_4$, or an unsubstituted or substituted alkyl, aryl or aralkyl group which preferably contains up to 20 carbon atoms in total (e.g., methyl group, ethyl group, methoxyethyl group, phenyl group, hydroxyethyl group, nitrophenyl group, chlorophenyl group, methoxyphenyl group, benzyl group, phenetyl group, etc.). Among these groups, particularly preferable $R^2$ is hydrogen atom.

Specific examples of the compounds represented by the general formula (I) are described below.

Compound (1): 1-(2-Hydroxyphenyl)-5-mercaptotetrazole.

Compound (2): 1-(3-Hydroxyphenyl)-5-mercaptotetrazole,

Compound (3): 1-(4-Hydroxyphenyl)-5-mercaptotetrazole,

Compound (4): 1-(2-Hydroxy-4-carboxyphenyl)-5-mercaptotetrazole,
Compound (5): 1-(3-Carboxy-4-hydroxyphenyl)-5-mercaptotetrazole,
Compound (6): 1-(3-Methoxycarbonyl-4-hydroxyphenyl)-5-mercaptotetrazole,
Compound (7): 1-(2,5-Dihydroxyphenyl)-5-mercaptotetrazole,
Compound (8): 1-(3,4,5-Trihydroxyphenyl)-5-mercaptotetrazole,
Compound (9): 1-(4-Hydroxyphenyl)-5-(2-methylcarbonylethylthio)tetrazole,
Compound (10): 1-(4-Hydroxyphenyl)-5-methoxycarbonylthiotetrazole.

These compounds can be obtained by firstly preparing

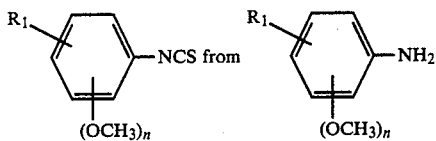

using a known method, e.g., the reaction with phosgene, and then, by reacting the resulting isothiocyanate with sodium azide. For details of the reaction procedures in the above-described synthesis descriptions in British Pat. No. 1,275,701, U.S. Pat. No. 3,266,897, and further, G. Dubenko & V. D. Panchenco, *j. Khim. Geterotsikl. Soedim.*, Sb-1; C. F. H. Allen, *Azots oder Zhaschie Geterotsikly*, pp. 199–201 (1967); *Can. J. Chem.*, vol. 44, p. 2315 (1966); *J. Indian Chem. Soc.*, vol. 58, p. 1087 (1981); and so on should be referred to.

The synthesis of the above-described compounds is illustrated below.

Synthesis Example 1

Synthesis of Compound (2): Sodium azide was dissolved in water in an amount corresponding to 1.2 equivalent to 3-methoxyphenylisothiocyanate, and cooled. Thereto, 3-methoxyphenylisothiocyanate was slowly added dropwise. Thereafter, the mixture was refluxed for 4 hours. After cooling, the reaction mixture was neutralized to precipitate crystals of 1-(3-methoxyphenyl)-5-mercaptotetrazole.

1-(3-Methoxyphenyl)-5-mercaptotetrazole was reacted with boron tribromide in methylene chloride to produce 1-(3-hydroxyphenyl)-5-mercaptotetrazole. Colorless Crystal. m.p. 176°–178° C.

Synthesis Example 2

Synthesis of Compound (5): 0.1 mole of sodium azide was dissolved in water, and while the resulting solution was cooled in an ice water bath, the equimolecular amount of methyl-2-methoxy-5-isocyanate benzoate was added thereto. The mixture was refluxed for 4 hours as heat was applied thereto. Thereafter, it was cooled and then, neutralized with HCl to produce 1-(3-methoxycarbonyl-4-methoxyphenyl)-5-mercaptotetrazole. 0.1 mole portion of the thus obtained compound was weighed out and dissolved in methylene chloride. The solution was cooled in an ice water bath and thereto, 0.3 mole of boron tribromide was added dropwise. The reaction mixture was stirred at 50° C. for 3 hours and then, 200 ml of water was poured thereinto. After removal of methylene chloride by distillation, 200 ml of a 5N sodium hydroxide aqueous solution was added, and heated at 70° C. for 2 hours. After cooling, the reaction mixture was neutralized with dilute hydrochloric acid to produce colorless crystals of Compound (5).

Synthesis Example 3

Synthesis of Compound (7): Sodium azide was dissolved in water in an amount corresponding to 1.1 equivalent to 2,5-dimethoxyphenylisothiocyanate, and cooled. Thereto, 2,5-dimethoxyphenylisothiocyanate was slowly added. After the conclusion of the addition, the mixture was stirred at a room temperature for 30 minutes and then, it was refluxed for 4 hours as heat was applied thereto. At the conclusion of the reaction, the reaction mixture was cooled and neutralized to produce crystals of 1-(2,5-dimethoxyphenyl)-5-mercaptotetrazole.

0.01 mole portion of the thus produced 1-(2,5-dimethoxyphenyl)-5-mercaptotetrazole was dissolved in methylene chloride, and cooled. Thereto, 0.02 mole of boron tribromide was added dropwise. After the conclusion of the reaction, water was added to the reaction mixture, the solvent was removed therefrom by distillation, and the product was extracted with ethyl acetate. After removal of the extracting solvent, the resulting product was dissolved again in ethyl acetate and therefrom, the product was recrystallized. Colorless crystal. m.p. 180° C. (decomposed).

Synthesis Example 4

Synthesis of Compound (8): 0.1 mole of 3,4,5-trimethoxyphenylisothiocyanate and the equimolecular amount of sodium azide were added to water while being cooled in an ice water bath.

The reaction mixture was heated and refluxed for 4 hours and then, cooled and neutralized to produce 1-(3,4,5-trimethoxyphenyl)-5-mercaptotetrazole. Next, 0.01 mole portion of the thus obtained compound was weighed out and dissolved in methylene chloride and thereto, 0.3 mole of boron tribromide was added dropwise. After continueing stirring for 5 hours, water was added to the reaction product. Crystals separating out were thoroughly washed with water, and recrystallized from ethanol. Then, Compound (8) was obtained as colorless crystals.

Other compounds can also be synthesized according to the above-described methods.

In the development-processing method of this invention, the procedure of developing an optically exposed silver halide photographic material with one of various kinds of known developing solutions is carried out in the presence of one of the above-described compounds represented by the general formula (I) of this invention. There are various means of making the compound of this invention be present at the time of development. However, it is desirable that the compound of this invention is incorporated in a sensitive material, especially in an emulsion layer thereof or in another hydrophilic colloidal layer thereof, during production, or added to a developing solution or to a pre-bath to be used before the development-processing.

The compounds of this invention can be added in a form of solution dissolved in water or appropriate solvents miscible with water (e.g., alcohols, ethers, glycols, ketones, esters, amides, etc.).

The compounds of this invention are preferably used in such an amount as to produce a fog-inhibiting effect. Specifically, a preferred addition amount in a sensitive material ranges from $10^{-7}$ to $10^{-2}$ mole, particularly from $10^{-6}$ to $10^{-2}$ mole of compound per mole of silver. A preferred concentration of the compound in a developing solution or in its pre-bath ranges from $10^{-6}$ to $10^{-1}$ mole/l, particularly from $10^{-5}$ to $3 \times 10^{-2}$ mole/l.

The development-processing method of this invention is carried out using the same developing solutions as known ones in the same processing manner as usual except that the compounds of this invention are present. However, lithographic developing solutions (the socalled infectious developing solutions) can not be employed in this invention. Namely, such developing solutions as to contain only dihydroxybenzenes as a developing agent and that, to contain a sulfite preservative at a concentration of 5 g/l or less can not be employed in this invention.

Suitable processing temperatures are usually selected from the range of 18° C. to 50° C. However, processing temperatures lower than 18° C. or higher than 50° C. may also be employed. Suitable processing times, though they depend on processing temperatures used, are usually selected from the range of 10 seconds to 12 minutes.

The method of this invention can be effective in any development-processing, whether it is a development-processing for producing a silver image (black-and-white photographic processing) or that for producing a dye image (color photographic processing), to be employed depending upon the end-use purpose of the sensitive material to be processed.

Developing solutions to be used in the case of black-and-white photographic processing can contain known developing agents. Specific examples of developing agents which can be used include dihydroxybenzenes (e.g., hydroquinone), 3-pyrazolidones (e.g., 1-phenyl-3-pyrazolidone), aminophenoles (e.g., N-methyl-p-aminophenol), 1-phenyl-3-pyrazolines, ascorbic acid, such heterocyclic compounds as to be formed by condensation of a 1,2,3,4-tetrahydroquinoline ring and an indolene ring which are described in U.S. Pat. No. 4,067,872, and so on. These developing agents can be used individually or in a combination of two or more thereof. However, only dihydroxybenzenes can not be used independently. In addition to the above-described developing agents, a developing solution may contain a generally known preservative, alkali agent, pH buffering agent, antifoggant and optionally, dissolving aid, color toning agent, development accelerating agent, surface active agent, defoaming agent, water softener, hardener, viscosity imparting agent and so on.

Fixing solutions which can be used are those having generally used compositions. Fixing agents which can be used therein include not only thiosulfates and thiocyanates, but also such organic sulfur compounds which are known to have a fixing effect. The fixing solutions may contain water soluble aluminium salts as a hardener.

On the other hand, dye images also can be formed using conventional processes. Specifically, the negative-positive process (described in, e.g., Journal of the Society of Motion Picture and Television Engineers, vol. 61, pp. 667–701 (1953)); the color reversal process in which negative silver image is firstly formed by development using a developing solution containing a black-and-white developing agent and then, uniform exposure is carried out at least once or another fogging treatment is carried out, followed by color development to produce positive dye image; the silver dye bleach process in which after exposure dye-containing photographic emulsion layers are developed to produce silver image, and dyes are bleached utilizing the thus produced silver image as a bleaching catalyst; and so on can be employed.

Color developing solutions are generally alkaline aqueous solutions containing color developing agents. Suitable color developing agents which can be used include known primary aromatic amine developers, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonylamidoethylaniline, 4-amino-3-methyl-N-ethyl-N-β-methoxyethylaniline, etc.).

In addition, those described in L. F. A. Mason, *Photographic Processing Chemistry*, pp. 226–229, Focal Press, London (1966); U.S. Pat. Nos. 2,193,015 and 2,592,364; published unexamined Japanese Patent Application 64933/'73; and so on may also be used as color developing agents.

The color developing solutions can additionally contain pH buffering agents such as the sulfites, the carbonates, the borates and the phosphates of alkali metals; development restrainers or antifoggants such as bromides, iodides and organic antifoggants; and so on. Optionally, they may contain water softeners; preservatives like hydroxylamine; organic solvents such as benzyl alcohol and diethylene glycol; development accelerators such as polyethylene glycol, quaternary ammonium salts and amines; dye forming couplers; competing couplers; fogging agents like sodium borohydride; auxiliary developers like 1-phenyl-3-pyrazolidones; viscosity imparting agents; chelating agents of polycarboxylic acid type described in U.S. Pat. No. 4,083,723; antioxidants described in West German Patent Application (OLS) 2,622,950; and so on.

After color development, photographic emulsion layers are usually subjected to a bleach-processing. The bleach-processing and the fixation-processing may be carried out simultaneously, or separately. Suitable bleaching agents which can be used include the compounds of polyvalent metals such as Fe (III), Co (III), Cr (VI), Cu (II) and so on; peroxy acids; quinones; nitroso compounds; and so on. More specifically, ferricyanides; dichromates; complex salts of Fe (III) or Co (III) and organic acids such as ethylenediamine tetraacetic acid, nitrilotriacetic acid, 1,3-diamino-2-propanol tetraacetic acid and other polycarboxylic acids, citric acid, tartaric acid, malic acid and so on; persulfates; permanganates; nitrosophenol; and so on can be used as the bleaching agent. Among these compounds, potassium ferricyanide, sodium ethylenediaminetetraacetatoferrate (III) and ammonium ethylenediaminetetraacetatoferrate (III) are particularly advantageous. Especially, ethylenediaminetetraacetatoiron (III) complex salts are employed to advantage in both an independent bleaching solution and a combined bleaching and fixing solution.

To a bleaching or a bleaching and fixing solution, bleach accelerating agents described in U.S. Pat. Nos. 3,042,520 and 3,241,966, published examined Japanese Patent Applications 8506/'70 and 8836/'70 and so on; thiol compounds described in published unexamined Japanese Patent Application 65732/'78; and various additives can be added.

The development-processing method of this invention can be applied to various kinds of known silver halide photographic materials.

Silver halide emulsions to which this invention can be applied include silver chloride, silver bromide, silver chlorobromide, silver iodide, silver iodobromide and silver chloroiodobromide emulsions. These emulsions may be chemically sensitized with unstable sulfur-containing compounds, gold compounds or both of them. Further, the emulsions may be spectrally sensitized with cyanine dyes, merocyanine dyes or/and the like. Furthermore, it is desirable that the emulsions contain stabilizers and antifoggants described in *Research Disclosure*, No. 17643 (December 1978) in addition to the compounds of this invention.

In particular, it is preferable to incorporate azaindenes (e.g., 4-hydroxy-6-methyl-1,3,3a,7-tetrazaindene and the like) into the emulsions. Moreover, the emulsions or other layer-forming coating solutions can contain a wide variety of additives known in the photographic art, such as hardeners (e.g., formaline, mucochloric acid, etc.), surface active agents as a coating aid, latexes for the purpose of dimentional stabilization, brightening agents, color image-forming couplers, DIR couplers, color mixing inhibitors, ultraviolet absorbents, discoloration inhibitors, mordants and so on. Details of these additives are known to those skilled in the art as described in, e.g., *Research Disclosure*, No. 17643, pp. 22–31 (December 1978).

Since the development-processing method of this invention employs the above-described novel antifoggant, it makes it possible to substantially suppress developmental fog with a reduced sacrifice of sensitivity. Further it can produce such an effect even on sensitive materials stored under circumstances of high temperature and humidity without diminishing its effect. Therefore, the method of this invention can be advantageously applied to the development-processing of black-and-white sensitive materials for taking, black-and-white sensitive materials for printing, color negative films, color papers, color reversal films, X-ray films and so on.

The present invention will now be illustrated in greater detail by reference to the following examples. However, the scope of the invention is not limited to these examples.

EXAMPLE 1

A silver iodobromide gelatin emulsion containing 6 mole % of silver iodide (having a mean grain size of 0.8μ) was ripened by adding sodium thiosulfate and potassium chloroaurate thereto.

Then, to each portion of the thus ripened emulsion were added one of the compounds of this invention or one of the compounds for comparison, which are set forth in Table 1, and further, a stabilizing agent (4-hydroxy-6-methyl-1,3,3a,7-tetrazaindene), a coating aid (sodium dodecylbenzenesulfonate) and a hardener (2,4-dichloro-6-hydroxy-s-triazine). Each of the resulting coating compositions was coated on a cellulose triacetate support, and dried. Thus, Samples 1 to 14 were obtained. Each of these samples was exposed to light using a sensitometer through an optical wedge (for 1/20 second), developed with a MQ developing solution having the following composition at a temperature of 32° C. for 1 minute and then, fixed, washed, dried and subjected to measurements of photographic properties (sensitivity and fog) in conventional manners. Thus, results shown in Table 1 were obtained.

Therein, the sensitivity is represented as a logarithm of a reciprocal of an exposure amount necessary for attaining a density of 0.2 excluding fog, i.e., the standard point of optical density to determine sensitivity was fog+0.2, and the sensitivity in Table 1 is shown as a relative value calculated by taking the sensitivity of Sample 1 as 100.

| Composition of MQ Developing Solution: | |
|---|---|
| Metol | 1.55 g |
| Sodium Sulfite | 22.5 g |
| Hydroquinone | 6.0 g |
| Sodium Carbonate (Monohydrate) | 39.5 g |
| Potassium Bromide | 0.95 g |
| Water to make | 1 l |

TABLE 1

| Sample | Compound | Addition Amount (mol/mol Ag) | Fog Density | Relative Sensitivity |
|---|---|---|---|---|
| 1 | — | — | 0.25 | 100 |
| 2 | Compound 1 | $9.0 \times 10^{-5}$ | 0.10 | 95 |
| 3 | Compound 1 | $3.6 \times 10^{-4}$ | 0.06 | 91 |
| 4 | Compound 2 | $1.8 \times 10^{-4}$ | 0.09 | 92 |
| 5 | Compound 2 | $5.4 \times 10^{-4}$ | 0.06 | 82 |
| 6 | Compound 3 | $9.0 \times 10^{-5}$ | 0.13 | 95 |
| 7 | Compound 3 | $5.4 \times 10^{-4}$ | 0.07 | 80 |
| 8 | Compound 5 | $7.1 \times 10^{-4}$ | 0.08 | 85 |
| 9 | Compound 7 | $9.0 \times 10^{-4}$ | 0.11 | 90 |
| 10 | Compound 7 | $3.6 \times 10^{-4}$ | 0.08 | 80 |
| 11 | Compound 8 | $3.6 \times 10^{-4}$ | 0.09 | 88 |
| 12 | Comparative Compound (a) | $9.0 \times 10^{-5}$ | 0.10 | 80 |
| 13 | Comparative Compound (a) | $3.6 \times 10^{-4}$ | 0.07 | 65 |
| 14 | Comparative Compound (c) | $3.6 \times 10^{-4}$ | 0.08 | 76 |

Comparative Compound (a)

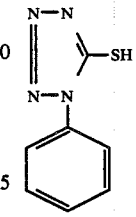

Comparative Compound (c)

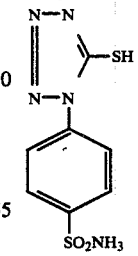

(They are the compounds described in U.S. Pat. No. 4,328,302)

As can be seen from Table 1, the compounds of this invention have an advantage that when they contribute to the suppression of developmental fog to the same extent as the comparative compound (a) of 1-phenyl-5-mercaptotetrazole, which is known to be a famous antifoggant, they cause less of a decrease in the sensitivity.

EXAMPLE 2

A silver iodobromide gelatin emulsion containing 1.5 mole % of silver iodide (a mean gain size of the silver halide: 0.9μ) was ripened by adding thereto potassium chloroaurate, ammonium rhodanide and sodium thiosulfate and heating the emulsion at 62° C. for 50 minutes. To each portion of the thus ripened emulsion, were added 3,3'-disulfopropyl-5,5'-diphenyl-9-ethyl-oxacarbocyanine sodium salt and then, one of the compounds of this invention or one of the comparative compounds set forth in Table 2 and further, the same stabilizing agent, coating aid and hardener as employed in Example 1. The thus prepared coating compositions were coated on separate films, and Samples 21 to 27 were obtained. A part of each sample was subjected to exposure just after coating using the same sensitometer as sued in Example 1, while the other part thereof was subjected to exposure in the same manner after the 3 days' storage in an atmosphere having a temperature of 50° C. and a relative humidity of 80%. They were development-processed at 35° C. for 35 second using a PQ developing solution having the composition described below, and subjected to measurements of photographic properties. Results thus obtained are shown in Table 2.

Therein, determination of sensitivity was carried out in the same manner as in Example 1, and the sensitivity is shown as a relative value obtained by taking the sensitivity of Sample 21 as 100.

| Composition of PQ Developing Solution: | |
|---|---|
| Sodium Sulfite | 40 g |
| Hydroquinone | 25 g |
| Boric Acid | 10 g |
| 1-Phenyl-3-pyrazolidone | 1.5 g |
| Potassium Hydroxide | 30 g |
| 5-Methylbenzotriazole | 0.15 g |
| Glutaraldehyde Bisulfite | 15 g |
| Acetic Acid | 12 g |
| Potassium Bromide | 10 g |
| Water to make | 1 l |

TABLE 2

| Sample | Compound | Addition Amount (mol/mol Ag) | Just After Coating | | After 3 Days' Storage (50° C., 80%) | |
|---|---|---|---|---|---|---|
| | | | Fog Density | Relative Sensitivity | Fog Density | Relative Sensitivity |
| 21 | — | — | 0.25 | 100 | 0.29 | 63 |
| 22 | Compound 1 | $2.8 \times 10^{-4}$ | 0.08 | 90 | 0.09 | 85 |
| 23 | Compound 3 | $5.4 \times 10^{-4}$ | 0.06 | 80 | 0.06 | 73 |
| 24 | Compound 5 | $9.0 \times 10^{-4}$ | 0.08 | 85 | 0.08 | 80 |
| 25 | Compound 7 | $3.6 \times 10^{-4}$ | 0.09 | 78 | 0.10 | 70 |
| 26 | Comparative Compound (a) | $2.1 \times 10^{-4}$ | 0.08 | 75 | 0.08 | 73 |
| 27 | Comparative Compound (b) | $1.8 \times 10^{-3}$ | 0.08 | 92 | 0.18 | 75 |

Comparative Compound (b)

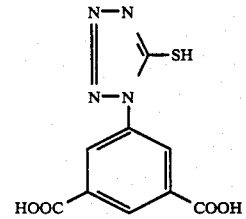

Comparative Compound (a) The same in Example 1.

As can be seen from Table 2, the compounds of this invention suppressed effectively generation of fog after storage under circumstances of high temperature and humidity, as well as just after the coating. Further, they controlled the decrease or the variation in sensitivity to relatively small levels.

On the other hand, the comparative compound (a) contributed to control of variations in fog density and sensitivity to be caused by storage under circumstances of high temperature and humidity to the same extent as the compounds of this invention. However, it caused a greater decrease in sensitivity when it attained suppression of fog generation.

In addition, the comparative compound (b) of 1-(3,5-dicarboxyphenyl)-5-mercaptotetrazole had a somewhat smaller decrease in sensitivity when suppression of fog generation was attained, compared with the compounds of this invention. However, the addition amount needed was considerably large, and the effect of suppressing fog generation under circumstances of high temperature and humidity was insufficient.

EXAMPLE 3

A silver iodobromide gelatin emulsion containing 7.5 mole % of silver iodide (a mean grain size of the silver halide: 0.6μ) was ripened by adding thereto potassium chloroaurate, ammonium rhodanide and sodium thiosulfate and heating the emulsion at 60° C. for 60 minutes.

Then, to each portion of the thus ripened emulsion were added one of the compounds of this invention or one of the compounds for comparison, which are set forth in Table 3, and further, the additives described below. Each of the resulting coating compositions was coated on a support, and dried. Thus, Samples 31 to 35 were prepared. Each of the samples was exposed to light through a yellow filter (for 1/20 second), subjected to the following color development processing and then, subjected to measurements of photographic properties. Thus, results shown in Table 3 were obtained.

Therein, determination of sensitivity was carried out in the same way as in Example 1, and the sensitivity is shown as a relative value obtained by taking the sensitivity of Sample 31 as 100.

| Color Development Processing: | |
|---|---|
| Step | Time |
| 1. Color Development | 3 min. 15 sec. (38° C.) |
| 2. Bleach | 6 min. 30 sec. |
| 3. Washing | 3 min. 15 sec. |
| 4. Fixation | 6 min. 30 sec. |
| 5. Washing | 3 min. 15 sec. |
| 6. Stabilization | 3 min. 15 sec. |

Compositions of processing solutions used in the above-described steps are described below.

| Composition of Color Developing Solution: | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—ethyl-N—β-hydroxyethylamino)-2-methyl-aniline Sulfate | 4.5 g |
| Water to make | 1 l |
| Composition of Bleaching Solution: | |
| Ammonium Bromide | 160.0 g |
| Ammonia Water (28%) | 25.0 ml |
| Sodium Ethylenediamine-tetraacetatoferrate (III) | 130 g |
| Glacial Acetic Acid | 14 ml |

-continued

| | | |
|---|---|---|
| Water to make | 1 l | |
| Composition of Fixing Solution: | | |
| Sodium Tetrapolyphosphate | 2.0 g | |
| Sodium Sulfite | 4.0 g | |
| Ammonium Thiosulfate (70% aq. soln.) | 175.0 ml | |
| Sodium Hydrogensulfite | 4.6 g | |
| Water to make | 1 l | |
| Composition of Stabilizing Solution: | | |
| Formaline | 8.0 ml | |
| Water to make | 1 l | |
| Additives: | | |
| Coupler: | 1-(2,4,6-Trichlorophenyl)-3-[3-(2,4-di-t-amylphenoxy)acetoamido]benzamido-5-pyrazolone. | |
| Spectral Sensitizer: | Sodium Salt of Bis-[2-{1-ethyl-3-(3-sulfopropyl)-5,6-dichlorobenz-imidazole}]trimethinecyanine. | |
| Stabilizer: | 4-Hydroxy-6-methyl-1,3,3a-7-tetrazaindene. | |
| Hardener: | Sodium Salt of 2,4-Dichloro-6-hydroxy-1,3,5-triazine. | |
| Coating Aid: | Mixture of Sodium p-Dodecylbenzene-sulfonate and Sodium p-Nonylphenoxy-poly(ethyleneoxy)propanesulfonate. | |

TABLE 3

| Sample | Compound | Addition Amount (mol/mol Ag) | Fog Density | Relative Sensitivity |
|---|---|---|---|---|
| 31 | — | — | 0.21 | 100 |
| 32 | Compound 1 | $5.4 \times 10^{-4}$ | 0.09 | 90 |
| 33 | Compound 1 | $1.2 \times 10^{-3}$ | 0.05 | 78 |
| 34 | Compound 2 | $1.8 \times 10^{-3}$ | 0.05 | 76 |
| 35 | Comparative Compound (a) | $5.4 \times 10^{-4}$ | 0.05 | 70 |

As can be seen from Table 3, the compounds of this invention showed desirable results with respect to color development in that they showed a smaller decrease in sensitivity than the comparative compound (a) while contributing to the suppresion of fog generation to similar extents.

EXAMPLE 4

In order to demonstrate effectiveness of the compounds of this invention when the compounds are added in developing solutions, the following experiment was carried out: Sample 1 prepared in Example 1 was exposed to light in the same manner as in Example 1, and developed with the same developing solution used in Example 1 except that one of the compounds of this invention or one of comparative compounds as set forth in Table 4 was added. Therein, the development temperature and a development time employed were 32° C. and 1 minute, respectively. Thereafter, photographic properties were examined in the same manner as in Example 1, and results set forth in Table 4 were obtained.

As can be seen from Table 4, the compounds of this invention showed desirable results in that they had less decrease in sensitivity than the comparative compound (a) when they contributed to suppression of fog generation to similar extents. The most striking aspect of this results is that some of the compounds actually brought about an increase in sensitivity.

TABLE 4

| Sample | Compound | Addition Amount (mole/liter) | Fog Density | Relative Sensitivity |
|---|---|---|---|---|
| 41 | — | — | 0.25 | 100 |
| 42 | Compound 1 | $3.3 \times 10^{-4}$ | 0.09 | 115 |
| 43 | Compound 1 | $1.0 \times 10^{-3}$ | 0.06 | 108 |
| 44 | Compound 2 | $3.3 \times 10^{-4}$ | 0.07 | 100 |
| 45 | Compound 2 | $1.0 \times 10^{-3}$ | 0.05 | 90 |
| 46 | Compound 3 | $1.0 \times 10^{-3}$ | 0.06 | 103 |
| 47 | Compound 5 | $1.0 \times 10^{-3}$ | 0.07 | 95 |
| 48 | Comparative Compound (a) | $1.5 \times 10^{-4}$ | 0.06 | 78 |
| 49 | Comparative Compound (a) | $3.3 \times 10^{-3}$ | 0.05 | 50 |
| 50 | Comparative Compound (c) | $3.3 \times 10^{-4}$ | 0.06 | 85 |

While the invention has been described in detail and with reference to specific embodiment thereof, it will be apparent to one skilled in the art that various changes and modifications can be made without departing from the spirit and scope thereof.

What is claimed is:

1. A method for development-processing an imagewise exposed silver halide photographic material having at least one light-sensitive silver halide emulsion layer on a support by forming a metal silver image on a black-and-white development-processing, comprising:
   development-processing the material by developing the material in the presence of a compound of the general formula I and in a development-processing solution selected from the groups consisting of:
   a solution containing both dihydroxybenzene and 3-pyrazolidones; and a solution containing both dihydroxybenzenes and aminophenoles;
   wherein the compound of the general formula (I) is:

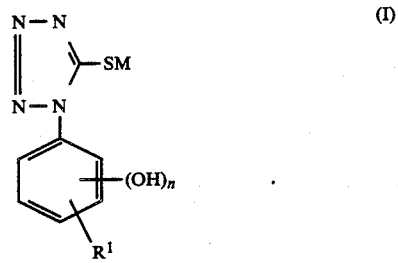

wherein M represents a hydrogen atom, an alkali metal atom, $NH_4$ or a mercapto group-protecting moiety which can be split-off in the presence of an alkali, said mercapto group-protecting moiety being $-COR^3$, $-COOR^3$, $-CH_2CH_2COOR^3$, $-CH_2CH_2COR^3$, $-CH_2CH_2CONR^3R^4$, $-CH_2CH_2CN$ or $-CH_2CH_2SO_2R^3$ wherein $R^3$ and $R^4$ each represents a hydrogen atom, or an unsubstituted alkyl, aryl or aralkyl group containing up to 20 carbon atoms in total; n represents 1, 2 or 3; $R^1$ represents a hydrogen atom or $-COOR^2$; and $R^2$ represents a hydrogen atom, an alkali metal atom, $NH_4$, or an unsubstituted or substituted alkyl, aryl or aralkyl group, the compound of general formula (I) being used in an amount sufficient to suppress the generation of development fog.

2. A method for development-processing as claimed in claim 1, wherein the alkali metal atom represented by M is Na or K.

3. A method for development-processing as claimed in claim 1, wherein M is said mercapto group-protecting moiety.

4. A method for development-processing as claimed in claim 1, wherein M represents a hydrogen atom, an alkali metal atom or NH$_4$.

5. A method for development-processing as claimed in claim 1, wherein n is 1 or 2.

6. A method for development-processing as claimed in claim 1, wherein the substituted or unsubstituted alkyl, aryl or aralkyl group represented by R$^2$ contains up to 20 carbon atoms in total.

7. A method for development-processing as claimed in claim 1, wherein R$^2$ is a hydrogen atom.

8. A method for development-processing as claimed in claim 1, wherein the compound of the general formula (I) is incorporated in the silver halide photographic material during the production of the material before image-wise exposure.

9. A method for development-processing as claimed in claim 1, wherein the compound of general formula (I) is present in the development-processing solution.

10. A method for development-processing as claimed in claim 1, further comprising the step of placing the material in a pre-bath prior to the development-processing solution and wherein the compound of the general formula (I) is present in the pre-bath.

11. A method for development-processing as claimed in claim 8, wherein the compound of general formula (I) is present in an amount of $10^{-7}$ to $10^{-2}$ mols per mole of silver.

12. A method for development-processing as claimed in claim 11, wherein the compound of general formula (I) is present in an amount in the range of $10^{-6}$ to $10^{-2}$ mol per mole of silver.

13. A method for development-processing as claimed in claim 9, wherein the compound of general formula (I) is present in the development-processing solution in an amount in the range of $10^{-6}$ to $10^{-1}$ mol/l.

14. A method for development-processing as claimed in claim 13, wherein the compound of general formula (I) is present in an amount in the range of from $10^{-5}$ to $3 \times 10^{-2}$ mol/l.

15. A method for development-processing as claimed in claim 10, wherein the compound of the general formula (I) is present in the pre-bath in an amount in the range of $10^{-6}$ to $10^{-1}$ mol/l.

16. A method for development-processing as claimed in claim 15, wherein the compound of general formula (I) is present in an amount in the range of $10^{-5}$ to $3 \times 10^{-2}$ mol/l.

17. A method for development-processing as claimed in claim 1, wherein the compound of general formula (I) is present in the development-processing solution or the pre-bath.

18. A method for development-processing an image-wise exposed silver halide photographic material having at least one light-sensitive silver halide emulsion layer on a support by forming a dye image by color development of a coupler with a color developing agent, comprising:

development-processing the material by developing the material in the presence of a compound of the general formula I and in a color development-processing solution containing a primary aromatic amine color developer, wherein the compound of the general formula (I) is:

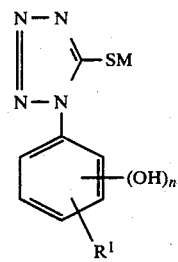

wherein M represents a hydrogen atom, an alkali metal atom, NH$_4$ or a mercapto group-protecting moiety which can be split-off in the presence of an alkali, said mercapto group-protecting moiety being —COR$^3$, —COOR$^3$, —CH$_2$CH$_2$COOR$^3$, —CH$_2$CH$_2$COR$^3$, —CH$_2$CH$_2$CONR$^3$R$^4$, —CH$_2$CH$_2$CN or —CH$_2$CH$_2$SO$_2$R$^3$ wherein R$^3$ and R$^4$ each represents a hydrogen atom, or an unsubstituted alkyl, aryl or aralkyl group containing up to 20 carbon atoms in total; n represents 1, 2 or 3; R$^1$ represents a hydrogen atom or —COOR$^2$; and R$^2$ represents a hydrogen atom, an alkali metal atom, NH$_4$, or an unsubstituted or substituted alkyl, aryl or aralkyl group, the compound of general formula (I) being used in an amount sufficient to suppress the generation of development fog.

19. A method for development-processing as claimed in claim 18, wherein the alkali metal atom represented by M is Na or K.

20. A method for development-processing as claimed in claim 18, wherein M is said mercapto group-protecting moiety.

21. A method for development-processing as claimed in claim 18, wherein M represents a hydrogen atom, an alkali metal atom or NH$_4$.

22. A method for development-processing as claimed in claim 18, wherein n is 1 or 2.

23. A method for development-processing as claimed in claim 18, wherein the substituted or unsubstituted alkyl, aryl, aralkyl group represented by R$^2$ contains up to 20 carbon atoms in total.

24. A method for development-processing as claimed in claim 18, wherein R$^2$ is a hydrogen atom.

25. A method for development-processing an image-wise exposed silver halide photographic material having at least one light-sensitive silver halide emulsion layer on a support by forming a dye image by color development of a coupler with a color developing agent, comprising:

development-processing the material by developing the material in the presence of a compound of the general formula I and in a color development-processing solution containing a primary aromatic amine color developer, wherein the compound of general formula I is incorporated in the material during the production of the material before image-wise exposure, and wherein the compound of the general formula (I) is:

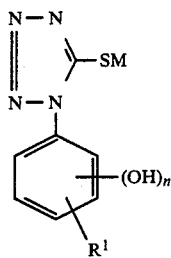

(I)

wherein M represents a hydrogen atom, an alkali metal atom, NH₄ or a mercapto group-protecting moiety which can be split-off in the presence of an alkali, said mercapto group-protecting moiety being —COR³, —COOR³, —CH₂CH₂COOR³, —CH₂CH₂COR³, —CH₂CH₂CONR³R⁴, —CH₂CH₂SO₂R³ wherein R³ and R⁴ each represents a hydrogen atom, or an unsubstituted alkyl, aryl or aralkyl group containing up to 20 carbon atoms in total; n represents 1, 2 or 3; R¹ represents a hydrogen atom or —COOR²; and R² represents a hydrogen atom, an alkali metal atom, NH₄, or an unsubstituted alkyl, aryl or aralkyl group, the compound of general formula (I) being used in an amount sufficient to suppress the generation of development fog.

26. A method for development-processing as claimed in claim 25, wherein the alkali metal atom represented by M is Na or K.

27. A method for development-processing as claimed in claim 25, wherein M is said mercapto group-protecting moiety.

28. A method for development-processing as claimed in claim 25, wherein M represents a hydrogen atom, an alkali metal atom or NH₄.

29. A method for development-processing as claimed in claim 25, wherein n is 1 or 2.

30. A method for development-processing as claimed in claim 25, wherein the substituted or unsubstituted alkyl, aryl, aralkyl group represented by R² contains up to 20 carbon atoms in total.

31. A method for development-processing as claimed in claim 25, wherein R² is a hydrogen atom.

32. A method for development-processing as claimed in claim 25, wherein the compound of general formula (I) is present in the material in an amount of $10^{-7}$ to $10^{-2}$ mols per mole of silver.

33. A method for development-processing as claimed in claim 25, wherein the compound of general foermula (I) is present in the material in an amount in the range of $10^{-6}$ to $10^{-2}$ mol per mole of silver.

34. A method for development-processing an imagewise exposed silver halide photographic material having at least one light-sensitive silver halide emulsion layer on a support by forming a dye image by color development of a coupler with a color developing agent, comprising:
development-processing the material by developing the material in the presence of a compound of the general formula I and in a color development-processing solution containing a primary aromatic amine color developer,
wherein the compound of general formula I is present during the developing as the result of (1) being incorporated in the color development-processing solution, or (2) placing the material in a pre-bath containing the compound of formula I prior to placing the material in the color development-processing solution, and wherein the compound of the general formula (I) is:

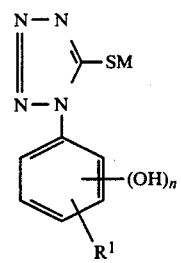

(I)

wherein M represents a hydrogen atom, an alkali metal atom, NH₄ or a mercapto group-protecting moiety which can be split-off in the presence of an alkali, said mercapto group-protecting moiety being —COR³, —COOR³, —CH₂CH₂COOR³, —CH₂CH₂COR³, —CH₂CH₂CONR³R⁴, —CH₂CH₂SO₂R³ wherein R³ and R⁴ each represents a hydrogen atom, or an unsubstituted alkyl, aryl or aralkyl group containing up to 20 carbon atoms in total; n represents 1, 2 or 3; R¹ represents a hydrogen atom or —COOR²; and R² represents a hydrogen atom, an alkali metal atom, NH₄, or an unsubstituted alkyl, aryl or aralkyl group, the compound of general formula (I) being used in an amount sufficient to suppress the generation of development fog.

35. A method for development-processing as claimed in claim 34, wherein the alkali metal atom represented by M is Na or K.

36. A method for development-processing as claimed in claim 34, wherein M is said mercapto group-protecting moiety.

37. A method for development-processing as claimed in claim 34, wherein M represents a hydrogen atom, an alkali metal atom or NH₄.

38. A method for development-processing as claimed in claim 34, wherein n is 1 or 2.

39. A method for development-processing as claimed in claim 34, wherein the substituted or unsubstituted alkyl, aryl, aralkyl group represented by R² contains up to 20 carbon atoms in total.

40. A method for development-processing as claimed in claim 34, wherein R² is a hydrogen atom.

41. A method for development-processing as claimed in claim 34, wherein the compound of general formula (I) is present in the color development-processing solution.

42. A method for development-processing as claimed in claim 34, wherein the compound of general formula (I) is present in the color development-processing solution in an amount in the range of $10^{-6}$ to $10^{-1}$ mol/liter.

43. A method for development-processing as claimed in claim 41, wherein the compound of general formula (I) is present in the color development-processing solution in an amount in the range of from $10^{-5}$ to $3 \times 10^{-2}$ mole/liter.

44. A method for development-processing as claimed in claim 34, wherein the compound of general formula I is present in the pre-bath.

45. A method for development-processing as claimed in claim 44, wherein the compound of the general formula (I) is present in the pre-bath in an amount in the range of $10^{-6}$ to $10^{-1}$ mol/liter.

46. A method for development-processing as claimed in claim 45, wherein the compound of general formula (I) is present in the pre-bath in an amount in the range of $10^{-5}$ to $3 \times 10^{-2}$ mol/liter.

* * * * *